(12) United States Patent
Tsai et al.

(10) Patent No.: US 9,764,153 B2
(45) Date of Patent: Sep. 19, 2017

(54) INTERCONNECT STRUCTURE AND METHOD OF FORMING SAME

(71) Applicant: Taiwan Semiconductor Manufacturing Company, Ltd., Hsin-Chu (TW)

(72) Inventors: Shu-Ting Tsai, Kaohsiung (TW); Jeng-Shyan Lin, Tainan (TW); Chun-Chieh Chuang, Tainan (TW); Dun-Nian Yaung, Taipei (TW); Jen-Cheng Liu, Hsin-Chu (TW); Feng-Chi Hung, Chu-Bei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/866,802

(22) Filed: Apr. 19, 2013

(65) Prior Publication Data

US 2014/0264883 A1    Sep. 18, 2014

Related U.S. Application Data

(60) Provisional application No. 61/784,139, filed on Mar. 14, 2013.

(51) Int. Cl.
*H01L 23/522* (2006.01)
*H01L 21/768* (2006.01)
(Continued)

(52) U.S. Cl.
CPC ......... *A61N 1/3931* (2013.01); *A61N 1/3987* (2013.01); *H01L 21/76898* (2013.01);
(Continued)

(58) Field of Classification Search
CPC ..... H01L 23/4952; H01L 24/05; H01L 24/30; H01L 24/33; H01L 2224/72625;
(Continued)

(56) References Cited

U.S. PATENT DOCUMENTS 6,593,645 B2 * 7/2003 Shih et al. .................... 257/686
6,740,567 B2   5/2004 Liang et al.
(Continued)

FOREIGN PATENT DOCUMENTS

CN      1738027 A    2/2006
CN    101794717 A    8/2010

*Primary Examiner* — Cheung Lee
*Assistant Examiner* — Stephen C Smith
(74) *Attorney, Agent, or Firm* — Slater Matsil, LLP

(57) ABSTRACT

A semiconductor device comprises a first chip bonded on a second chip. The first chip comprises a first substrate and first interconnection components formed in first IMD layers. The second chip comprises a second substrate and second interconnection components formed in second IMD layers. The device further comprises a first conductive plug formed within the first substrate and the first IMD layers, wherein the first conductive plug is coupled to a first interconnection component and a second conductive plug formed through the first substrate and the first IMD layers and formed partially through the second IMD layers, wherein the second conductive plug is coupled to a second interconnection component.

17 Claims, 16 Drawing Sheets

(51) Int. Cl.
*H01L 23/00* (2006.01)
*H01L 25/00* (2006.01)
*A61N 1/39* (2006.01)
*H01L 23/48* (2006.01)
*H01L 23/532* (2006.01)
*H01L 27/06* (2006.01)
*H01L 27/146* (2006.01)

(52) U.S. Cl.
CPC ...... *H01L 23/481* (2013.01); *H01L 23/53238* (2013.01); *H01L 25/50* (2013.01); *H01L 27/0688* (2013.01); *H01L 27/14634* (2013.01); H01L 23/53257 (2013.01); H01L 2224/08145 (2013.01); H01L 2224/80894 (2013.01); H01L 2224/80896 (2013.01); H01L 2224/9202 (2013.01); H01L 2224/94 (2013.01); H01L 2225/06513 (2013.01); H01L 2225/06541 (2013.01); *H01L 2924/1431* (2013.01)

(58) Field of Classification Search
CPC ............ H01L 23/481; H01L 23/53238; H01L 23/53257; H01L 25/50; H01L 27/0688; H01L 27/14634; H01L 2924/1431; H01L 2225/06513; H01L 2225/06541; A61N 1/3931; A61N 1/3987

USPC .................................................. 257/773–776
See application file for complete search history.

(56) References Cited

U.S. PATENT DOCUMENTS

| | | |
|---|---|---|
| 7,495,206 B2 * | 2/2009 | Park ........................... 250/214.1 |
| 8,022,493 B2 * | 9/2011 | Bang ............................. 257/440 |
| 8,076,234 B1 * | 12/2011 | Park et al. ..................... 438/622 |
| 8,501,587 B2 * | 8/2013 | Chen et al. ..................... 438/459 |
| 9,449,914 B2 * | 9/2016 | Ho ........................... H01L 24/24 |
| 2002/0197775 A1 * | 12/2002 | Liang et al. .................. 438/141 |
| 2003/0168744 A1 * | 9/2003 | Sawada et al. ............... 257/758 |
| 2003/0194872 A1 * | 10/2003 | Parikh ............... H01L 21/76805 438/694 |
| 2005/0286287 A1 * | 12/2005 | Park .................... G11C 11/5621 365/63 |
| 2006/0038300 A1 * | 2/2006 | Tanida et al. .................. 257/773 |
| 2006/0146233 A1 * | 7/2006 | Park ............................. 349/95 |
| 2006/0246710 A1 * | 11/2006 | Cheong ............. H01L 21/28562 438/618 |
| 2009/0104749 A1 * | 4/2009 | Sung et al. .................... 438/396 |
| 2010/0178761 A1 * | 7/2010 | Chen et al. .................... 438/613 |
| 2012/0056330 A1 * | 3/2012 | Lee .................. H01L 21/76898 257/774 |

* cited by examiner

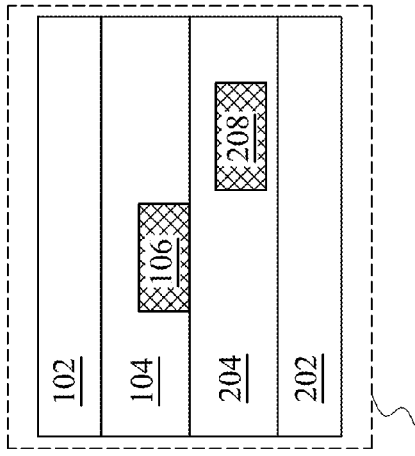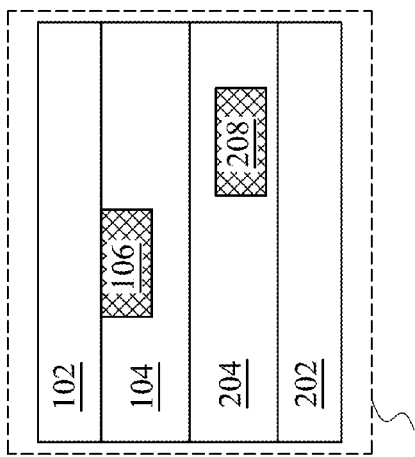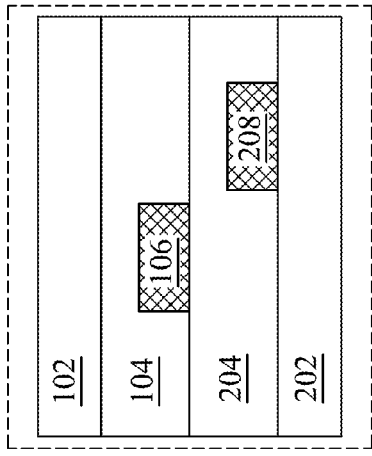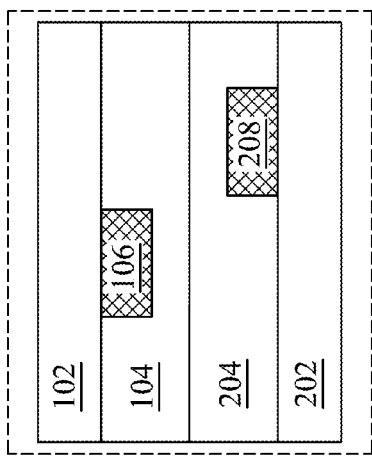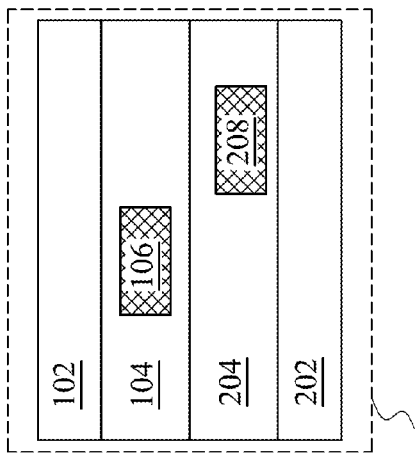
Fig. 15
Fig. 16

INTERCONNECT STRUCTURE AND METHOD OF FORMING SAME

CROSS REFERENCE TO RELATED APPLICATIONS

This application is related to, and claims priority to U.S. Provisional Application No. 61/784,139, titled, "Interconnect Structure and Method of Forming Same" filed on Mar. 14, 2013, which is herein incorporated by reference.

BACKGROUND

The semiconductor industry has experienced rapid growth due to continuous improvements in the integration density of a variety of electronic components (e.g., transistors, diodes, resistors, capacitors, etc.). For the most part, this improvement in integration density has come from repeated reductions in minimum feature size (e.g., shrink the semiconductor process node towards the sub-20 nm node), which allows more components to be integrated into a given area. As the demand for miniaturization, higher speed and greater bandwidth, as well as lower power consumption and latency has grown recently, there has grown a need for smaller and more creative packaging techniques of semiconductor dies.

As semiconductor technologies further advance, stacked semiconductor devices have emerged as an effective alternative to further reduce the physical size of a semiconductor device. In a stacked semiconductor device, active circuits such as logic, memory, processor circuits and the like are fabricated on different semiconductor wafers. Two or more semiconductor wafers may be installed on top of one another to further reduce the form factor of the semiconductor device.

Two semiconductor wafers may be bonded together through suitable bonding techniques. The commonly used bonding techniques include direct bonding, chemically activated bonding, plasma activated bonding, anodic bonding, eutectic bonding, glass frit bonding, adhesive bonding, thermo-compressive bonding, reactive bonding and/or the like. Once two semiconductor wafers are bonded together, the interface between two semiconductor wafers may provide an electrically conductive path between the stacked semiconductor wafers.

One advantageous feature of stacked semiconductor devices is much higher density can be achieved by employing stacked semiconductor devices. Furthermore, stacked semiconductor devices can achieve smaller form factors, cost-effectiveness, increased performance and lower power consumption.

BRIEF DESCRIPTION OF THE DRAWINGS

For a more complete understanding of the present invention, and the advantages thereof, reference is now made to the following descriptions taken in conjunction with the accompanying drawings, in which:

FIG. 15 illustrates a plurality of first combinations of the dual pads in accordance with various embodiments of the present disclosure;

FIG. 16 illustrates a plurality of second combinations of the dual pads in accordance with various embodiments of the present disclosure.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, a method for forming interconnect structures for a stacked semiconductor device. The invention may also be applied, however, to a variety of semiconductor devices. Hereinafter, various embodiments will be explained in detail with reference to the accompanying drawings.

Figure 1:
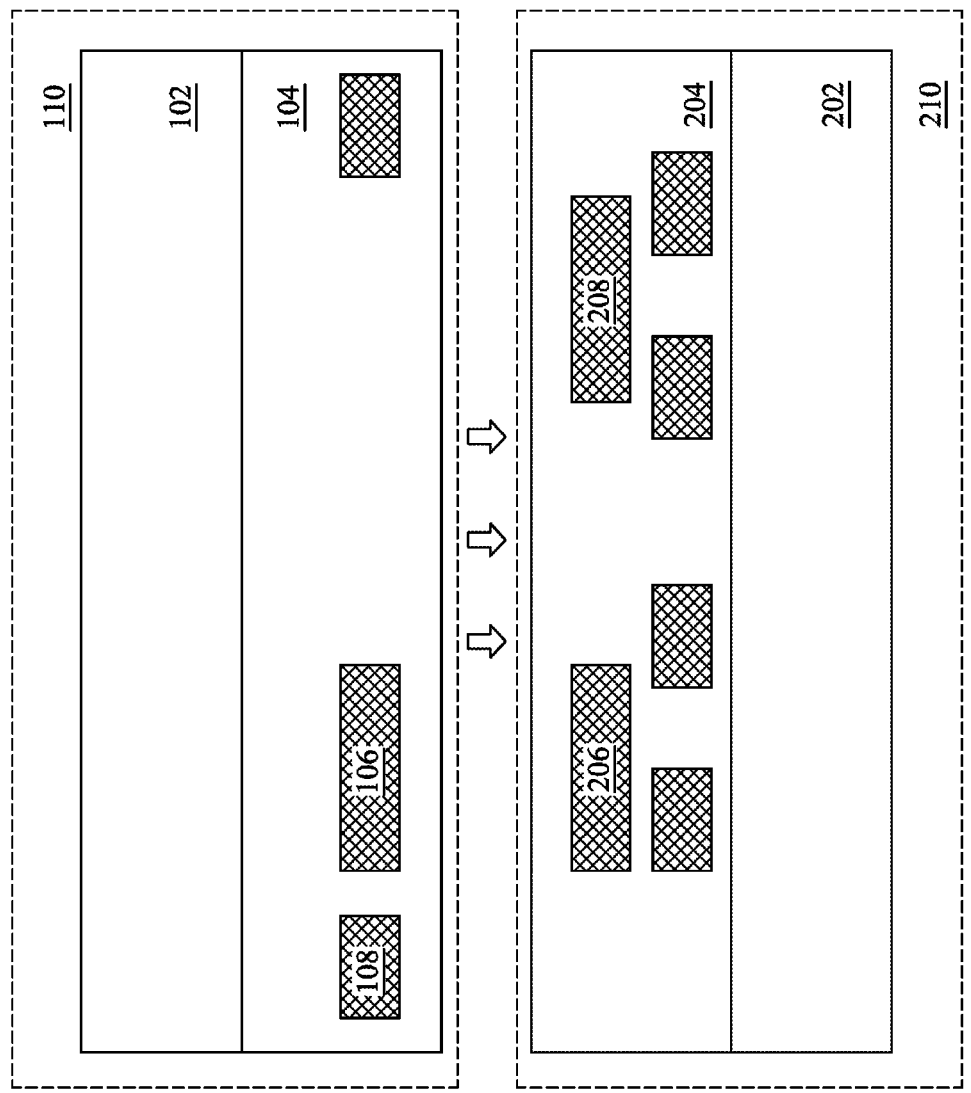
FIG. 1 illustrates a cross sectional view of a stacked semiconductor device prior to a bonding process in accordance with various embodiments of the present disclosure.

FIG. 1 illustrates a cross sectional view of a stacked semiconductor device prior to a bonding process in accordance with various embodiments of the present disclosure. Both the first semiconductor wafer 110 and the second semiconductor wafer 210 include a semiconductor substrate (e.g., first substrate 102 and second substrate 202) and a plurality of interconnect structures (e.g., metal lines 106, 108, 206 and 208) formed over the semiconductor substrate. The first semiconductor wafer 110 is used as an example to illustrate the detailed structure of the semiconductor wafers prior to a bonding process.

As shown in FIG. 1, the first semiconductor wafer 110 may comprises a first substrate 102 and a plurality of inter-metal dielectric layers 104 formed over the first substrate 102. In addition, a plurality of metal lines such as metal lines 106 and 108 are formed in the inter-metal dielectric layers 104.

The first substrate 102 may be formed of silicon, although it may also be formed of other group III, group IV, and/or group V elements, such as silicon, germanium, gallium, arsenic, and combinations thereof. The first substrate 102 may also be in the form of silicon-on-insulator (SOI). The SOI substrate may comprise a layer of a semiconductor material (e.g., silicon, germanium and/or the like) formed over an insulator layer (e.g., buried oxide and/or the like), which is formed in a silicon substrate. In addition, other substrates that may be used include multi-layered substrates, gradient substrates, hybrid orientation substrates, any combinations thereof and/or the like.

The first substrate 102 may further comprise a variety of electrical circuits (not shown). The electrical circuits formed on the first substrate 102 may be any type of circuitry suitable for a particular application. In accordance with some embodiments, the electrical circuits may include various n-type metal-oxide semiconductor (NMOS) and/or p-type metal-oxide semiconductor (PMOS) devices such as transistors, capacitors, resistors, diodes, photo-diodes, fuses and/or the like.

The electrical circuits may be interconnected to perform one or more functions. The functions may include memory structures, processing structures, sensors, amplifiers, power distribution, input/output circuitry and/or the like. One of ordinary skill in the art will appreciate that the above examples are provided for illustrative purposes only and are not intended to limit the various embodiments to any particular applications.

The inter-metal dielectric layers 104 are formed over the first substrate 102. As shown in FIG. 1, the inter-metal dielectric layers 104 may comprise a plurality of metal lines such as metal lines 106 and 108.

The metal lines 106 and 108 may be made through any suitable formation process (e.g., lithography with etching, damascene, dual damascene, or the like) and may be formed using suitable conductive materials such as copper, aluminum, aluminum alloys, copper alloys or the like.

As shown in FIG. 1, the first semiconductor wafer 110 will be stacked on top of the second semiconductor wafer 210. In some embodiments, a plurality of bonding pads are formed in the first semiconductor wafer 110 and the second semiconductor wafer 210 respectively. Furthermore, the bonding pads located at the second semiconductor wafer 210 are aligned face-to-face with their corresponding bonding pads located at the first semiconductor wafer 110. The first semiconductor wafer 110 and the second semiconductor wafer 210 are bonded together through suitable bonding techniques such as direct bonding.

In accordance with some embodiments, in a direct bonding process, the connection between the first semiconductor wafer 110 and the second semiconductor wafer 210 can be implemented through metal-to-metal bonding (e.g., copper-to-copper bonding), dielectric-to-dielectric bonding (e.g., oxide-to-oxide bonding), metal-to-dielectric bonding (e.g., oxide-to-copper bonding), any combinations thereof and/or the like.

It should be noted that the bonding show in FIG. 1 may be at wafer level. In the wafer-level bonding, wafers 110 and 210 are bonded together, and are then sawed into dies. Alternatively, the bonding may be performed at the chip level.

Figure 2:
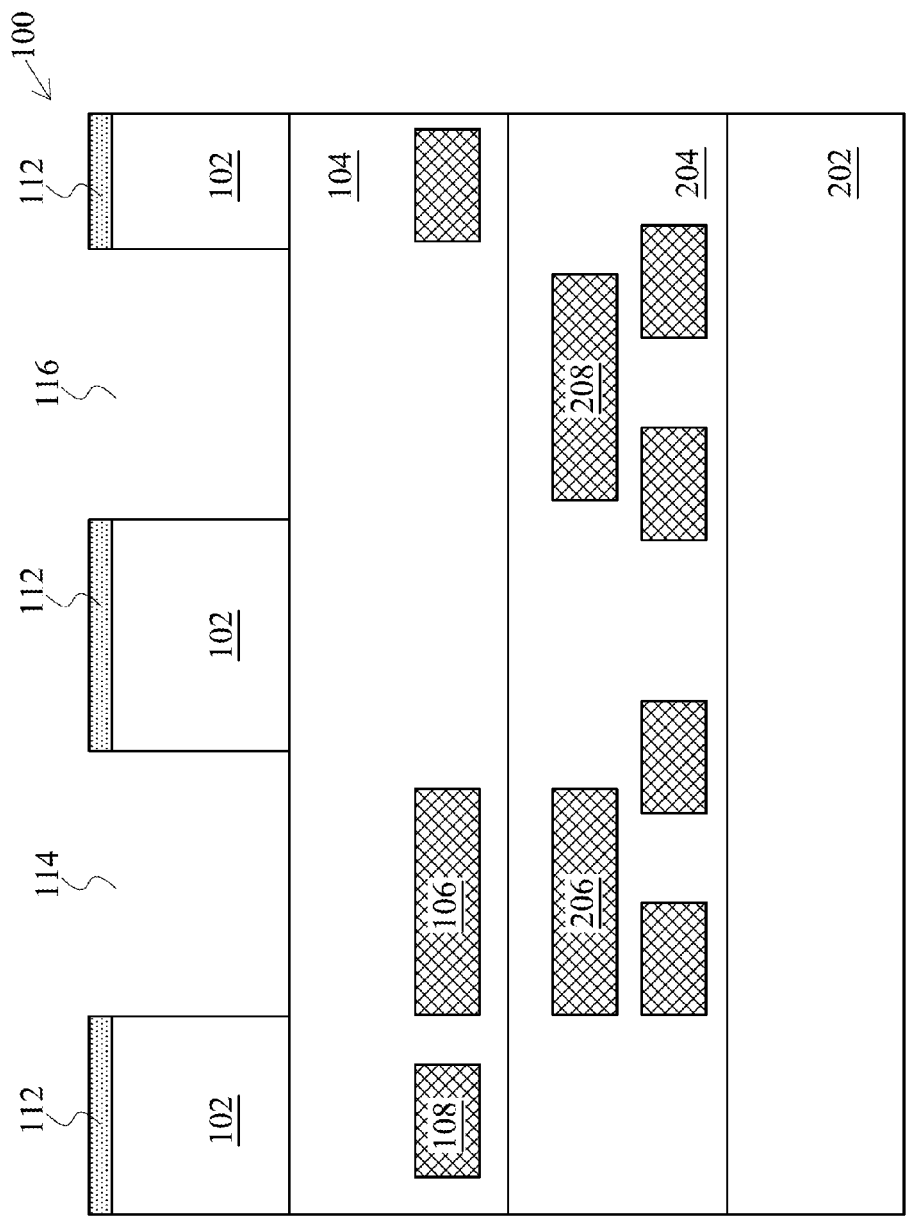
FIG. 2 illustrates a cross sectional view of the semiconductor device shown in FIG. 1 after a bottom anti-reflection coating (BARC) layer is formed over the first semiconductor wafer and a patterning process is applied to the substrate of the first semiconductor wafer in accordance with various embodiments of the present disclosure.

FIG. 2 illustrates a cross sectional view of the semiconductor device shown in FIG. 1 after a bottom anti-reflection coating (BARC) layer is formed over the first semiconductor wafer and a patterning process is applied to the substrate of the first semiconductor wafer in accordance with various embodiments of the present disclosure. The BARC layer 112 is formed on a backside of the first substrate 102. Throughout the description, the side of the first substrate 102 adjacent to the BARC layer 112 is referred to as the backside of the first substrate 102.

The BARC layer 112 may be formed of a nitride material, an organic material, an oxide material and the like. The BARC layer 112 may be formed using suitable techniques such as chemical vapor deposition (CVD) and/or the like.

A patterned mask such as a photoresist mask and/or the like may be formed over the BARC layer 112 using suitable deposition and photolithography techniques. A suitable etching process, such as a reactive ion etch (RIE) or other dry etch, an anisotropic wet etch, or any other suitable anisotropic etch or patterning process may be applied to the first substrate 102 of the first semiconductor wafer 110. As a result, a plurality of openings 114 and 116 are formed in the first substrate 102.

Figure 3:
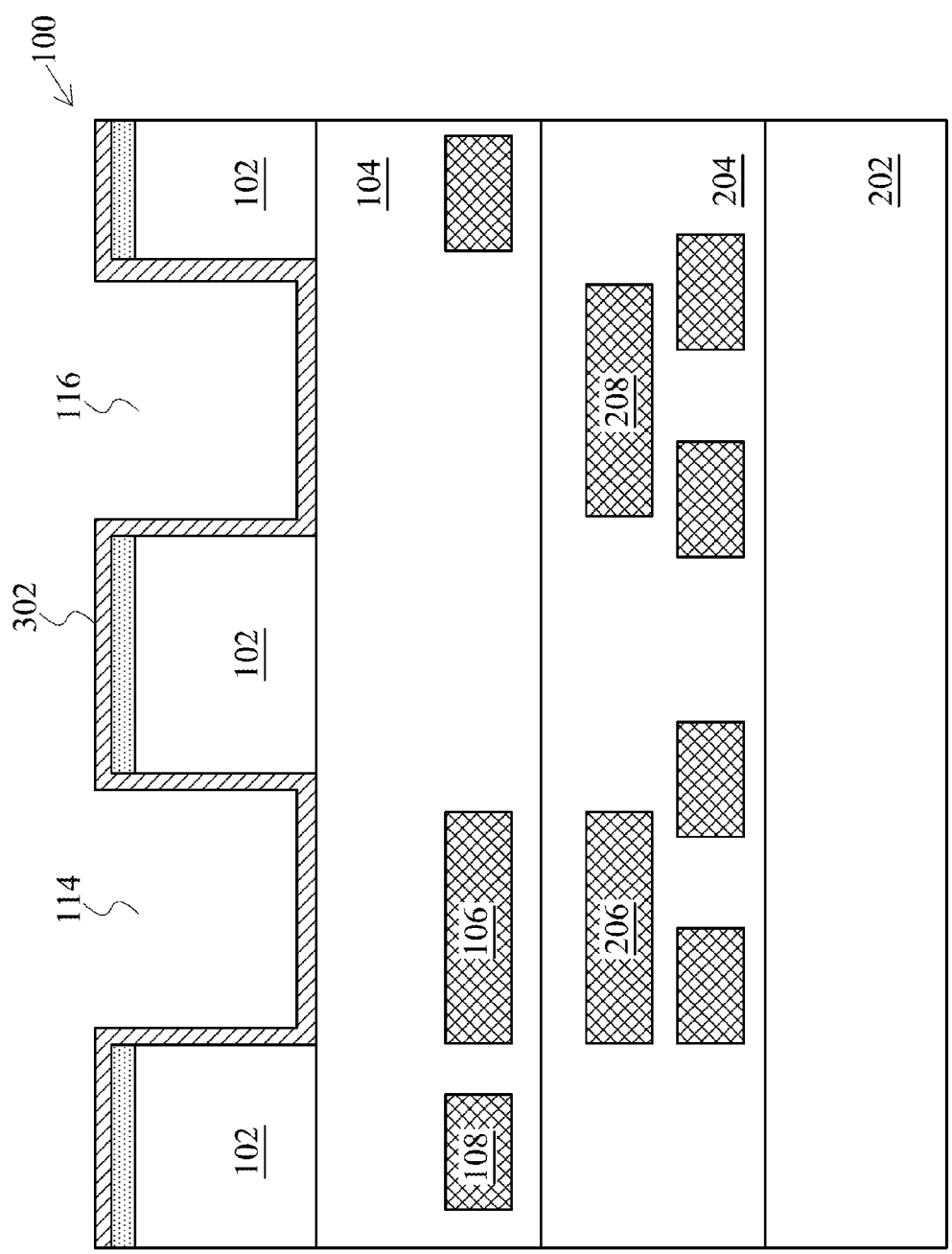
FIG. 3 illustrates a cross section view of the semiconductor device shown in FIG. 2 after a dielectric layer is deposited over the semiconductor device in accordance with various embodiments of the present disclosure.

FIG. 3 illustrates a cross section view of the semiconductor device shown in FIG. 2 after a dielectric layer is deposited over the semiconductor device in accordance with various embodiments of the present disclosure. As shown in FIG. 3, a dielectric layer 302 is formed over the bottoms and sidewalls of the openings 114 and 116. In addition, the dielectric layer 302 is formed over the BARC layer 112.

The dielectric layer 302 may be formed of various dielectric materials commonly used in integrated circuit fabrication. For example, the dielectric layer 302 may be formed of silicon dioxide, silicon nitride or a doped glass layer such as boron silicate glass and the like. Alternatively, dielectric layer may be a layer of silicon nitride, a silicon oxynitride layer, a polyamide layer, a low dielectric constant insulator or the like. In addition, a combination of the foregoing dielectric materials may also be used to form the dielectric layer 302. In accordance with some embodiments, the dielectric layer 302 may be formed using suitable techniques such as sputtering, oxidation, CVD and/or the like.

Figure 4:
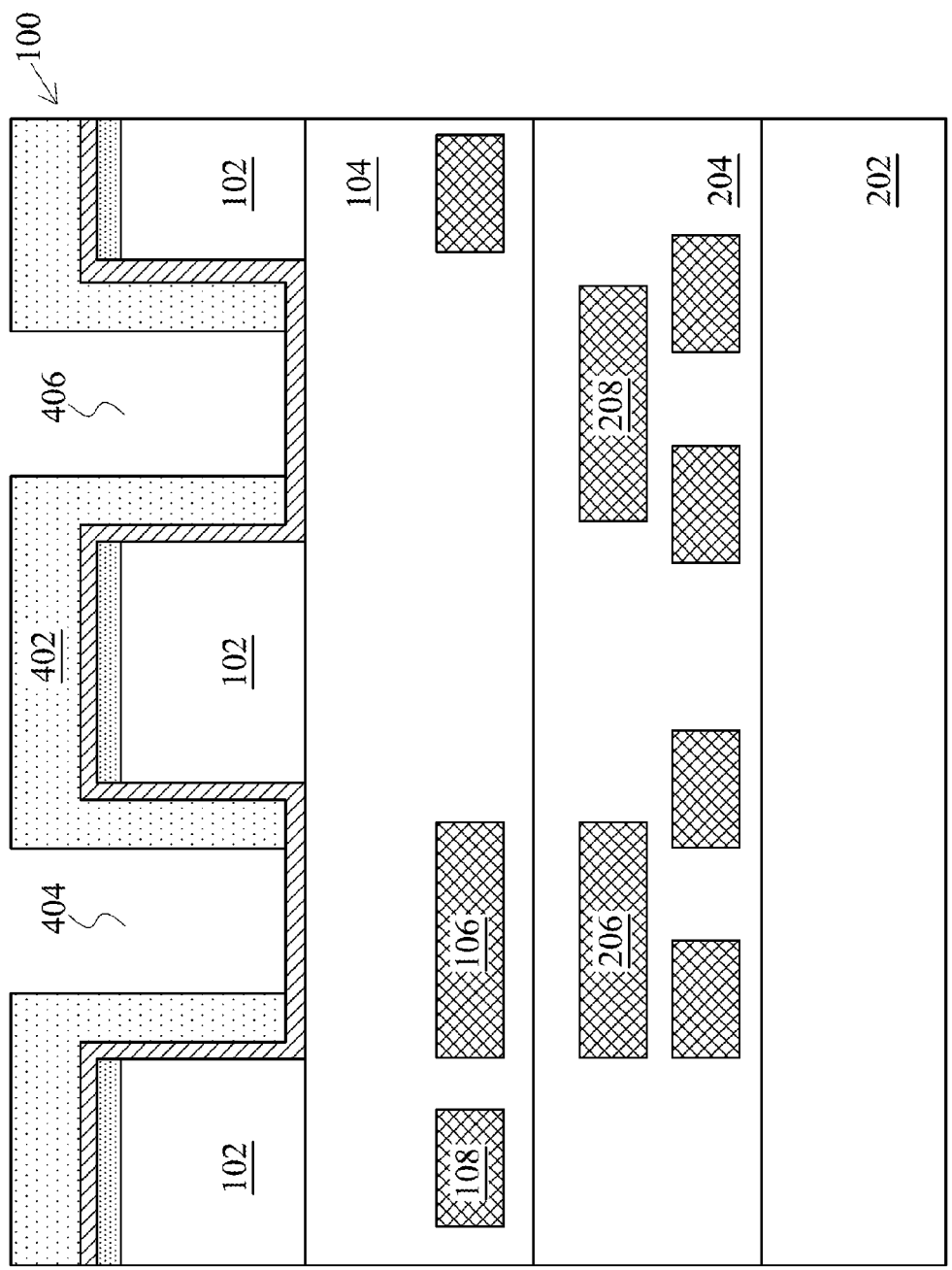
FIG. 4 illustrates a cross section view of the semiconductor device shown in FIG. 3 after a mask layer is formed over the semiconductor device in accordance with various embodiments of the present disclosure.

FIG. 4 illustrates a cross section view of the semiconductor device shown in FIG. 3 after a mask layer is formed over the semiconductor device in accordance with various embodiments of the present disclosure. A patterned mask 402 is formed over the sidewalls of the openings 114 and 116 (shown in FIG. 3). As shown in FIG. 4, two new openings 404 and 406 are formed after the patterned mask 402 are formed along the sidewalls of the openings 114 and 116.

The patterned mask 402 may be a photoresist layer. The patterned mask 402 is formed on the top surface of the semiconductor device using suitable deposition and photolithography techniques.

Figure 5:
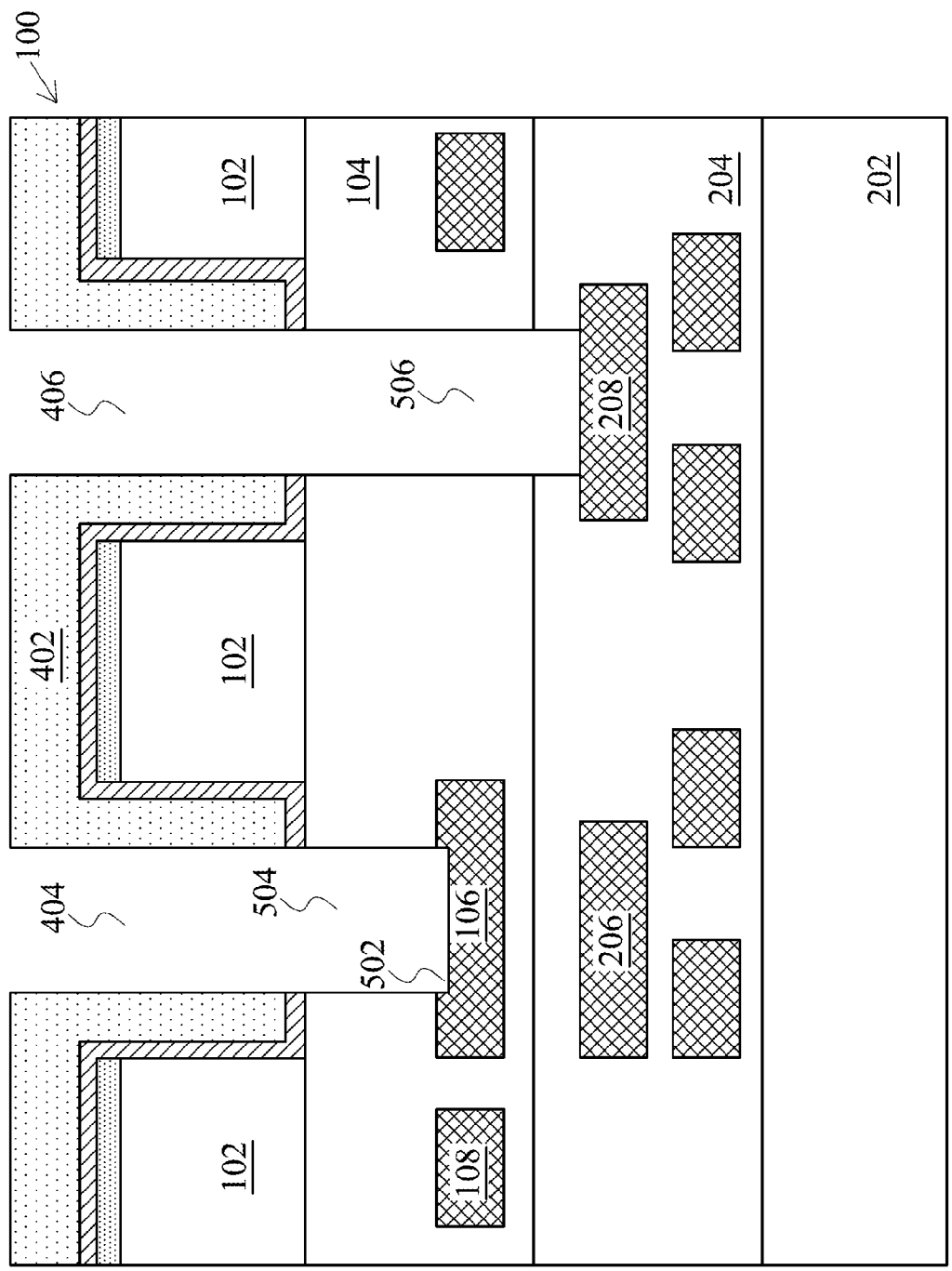
FIG. 5 illustrates a cross section view of the semiconductor device shown in FIG. 4 after an etching process is applied to the semiconductor device in accordance with various embodiments of the present disclosure.

FIG. 5 illustrates a cross section view of the semiconductor device shown in FIG. 4 after an etching process is applied to the semiconductor device in accordance with various embodiments of the present disclosure. A suitable etching process, such as a dry etch, an anisotropic wet etch, or any other suitable anisotropic etch or patterning process, may be performed to form openings 504 and 506. The openings 504 and 506 are respective extensions of the openings 404 and 406. In particular, the opening 506 extends through the inter-metal dielectric layer 104 and the bonding interface of two stacked wafers, and extends partially into the inter-metal dielectric layer 204. In contrast, the opening 504 extends partially into the inter-metal dielectric layer 104. As shown in FIG. 5, the metal lines 106 and 208 are exposed after the openings 504 and 506 have been formed.

It should be noted that the metal line 106 may be formed of suitable metal materials such as copper, which is of a different etching rate (selectivity) from the first substrate 102 and the inter-metal dielectric layers. As such, the metal line 106 may function as a hard mask layer for the etching process of the inter-metal dielectric layers 104 and 204. A selective etching process may be employed to etch the inter-metal dielectric layers 104 and 204 rapidly while etching only a portion of the metal line 106. As shown in FIG. 5, the exposed portion of the hard mask layer (e.g., metal line 106) is partially etched away, thereby forming a recess such as recess 502. The depth of the recess 502 may vary depending on different applications and design needs.

Figure 6:
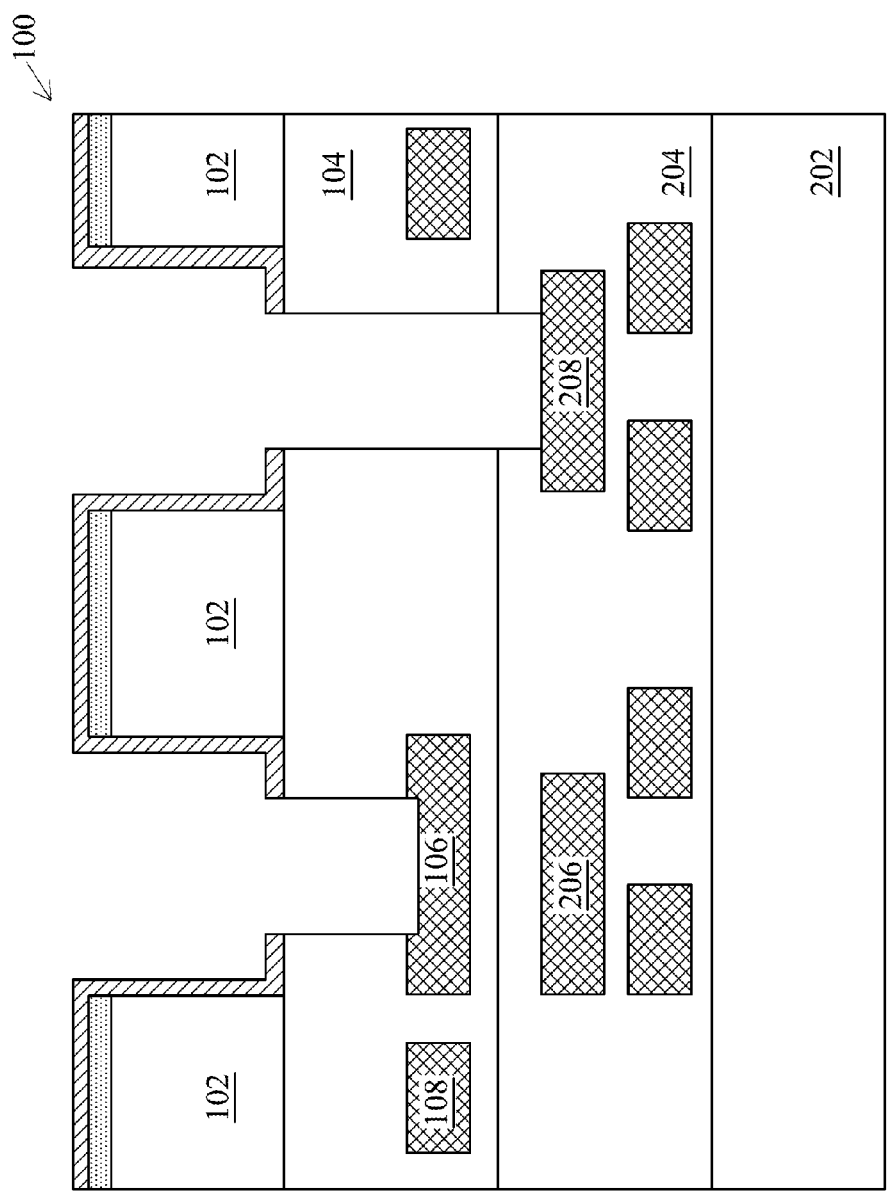
FIG. 6 illustrates a cross sectional view of the semiconductor device shown in FIG. 5 after the remaining photoresist layer has been removed in accordance with various embodiments of the present disclosure.

FIG. 6 illustrates a cross sectional view of the semiconductor device shown in FIG. 5 after the remaining photoresist layer has been removed in accordance with various embodiments of the present disclosure. The remaining photoresist layer shown in FIG. 5 may be removed by using suitable photoresist stripping techniques such as chemical solvent cleaning, plasma ashing, dry stripping and/or the like. The photoresist stripping techniques are well known and hence are not discussed in further detail herein to avoid repetition.

Figure 7:
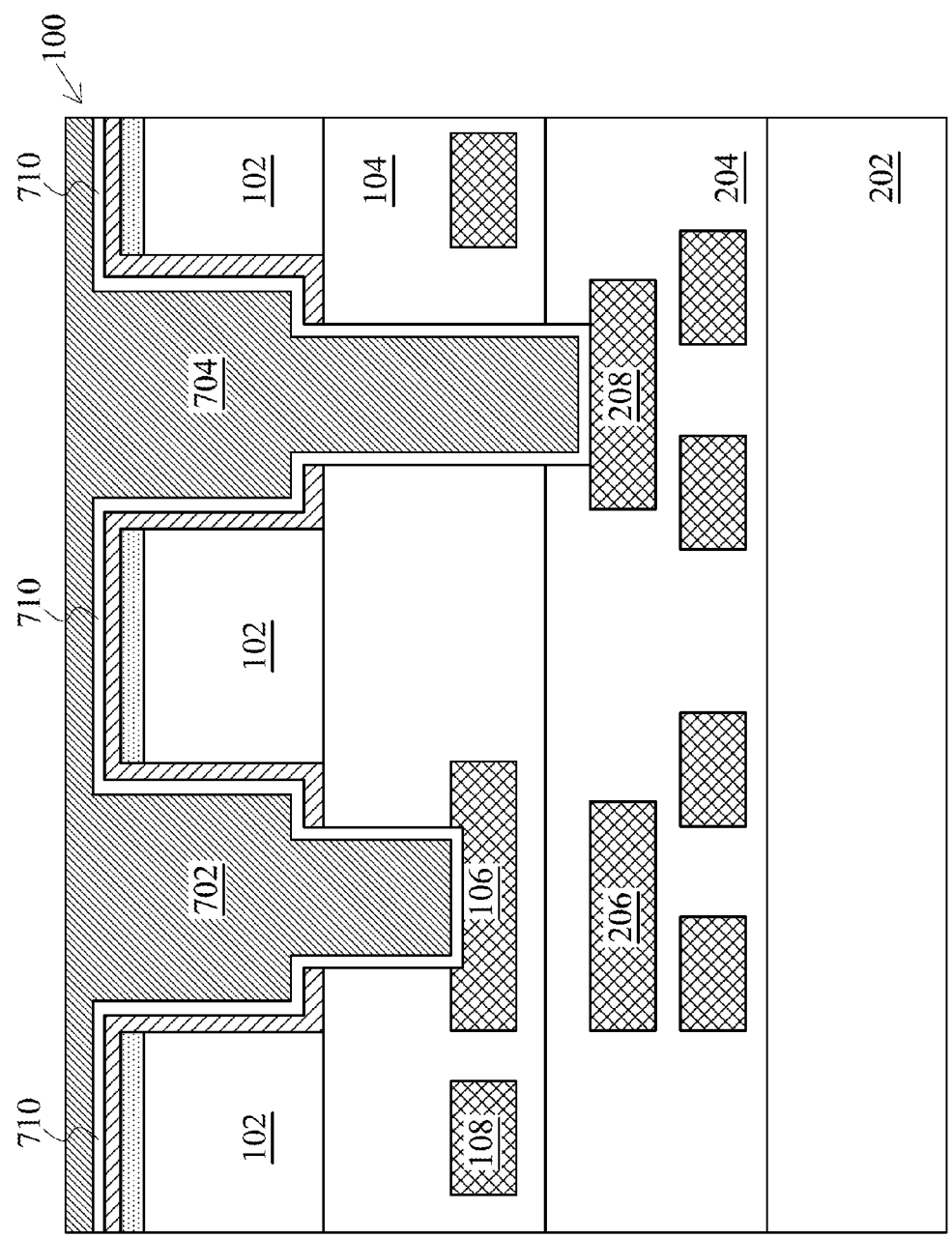
FIG. 7 illustrates a cross sectional view of the semiconductor device shown in FIG. 6 after a conductive material has been filled in the openings in accordance with various embodiments of the present disclosure.

FIG. 7 illustrates a cross sectional view of the semiconductor device shown in FIG. 6 after a conductive material has been filled in the openings in accordance with various embodiments of the present disclosure. In some embodiments, a barrier layer and a seed layer may be deposited prior to a plating process, through which the conductive material is filled into the openings.

A barrier layer 710 may be deposited on the bottom as well as the sidewalls of the opening (e.g., opening 404 shown in FIG. 6). The barrier layer 710 may be formed of titanium, titanium nitride, tantalum, tantalum nitride, and combinations thereof and/or the like. In some embodiments, the barrier layer 710 may be uniform in thickness. In alternative embodiments, the barrier layer 710 may be non-uniform in thickness. The barrier layer 710 may be formed using suitable fabrication techniques such as atomic layer deposition (ALD), plasma enhance CVD (PECVD), plasma enhanced physical vapor deposition (PEPVD) and/or the like.

In addition, a seed layer (not shown) may be deposited over the barrier layer 710. The seed layer may be may be formed of copper, nickel, gold, any combination thereof and/or the like. The seed layer may be formed by suitable deposition techniques such as PVD, CVD and/or the like.

Moreover, the seed layer may be alloyed with a material that improves the adhesive properties of the seed layer so that it can act as an adhesion layer. For example, the seed layer may be alloyed with a material such as manganese or aluminum, which will migrate to the interface between the seed layer and the barrier layer 710 and will enhance the adhesion between these two layers. The alloying material may be introduced during formation of the seed layer. The alloying material may comprise no more than about 10% of the seed layer.

Once the barrier layer 710 and the seed layer has been deposited in the openings, a conductive material, which includes tungsten, titanium, aluminum, copper, any combinations thereof and/or the like, is filled into the openings, forming conductive plugs 702 and 704. In some embodiments, the conductive material may be filled in the openings through an electroplating process.

Figure 8:
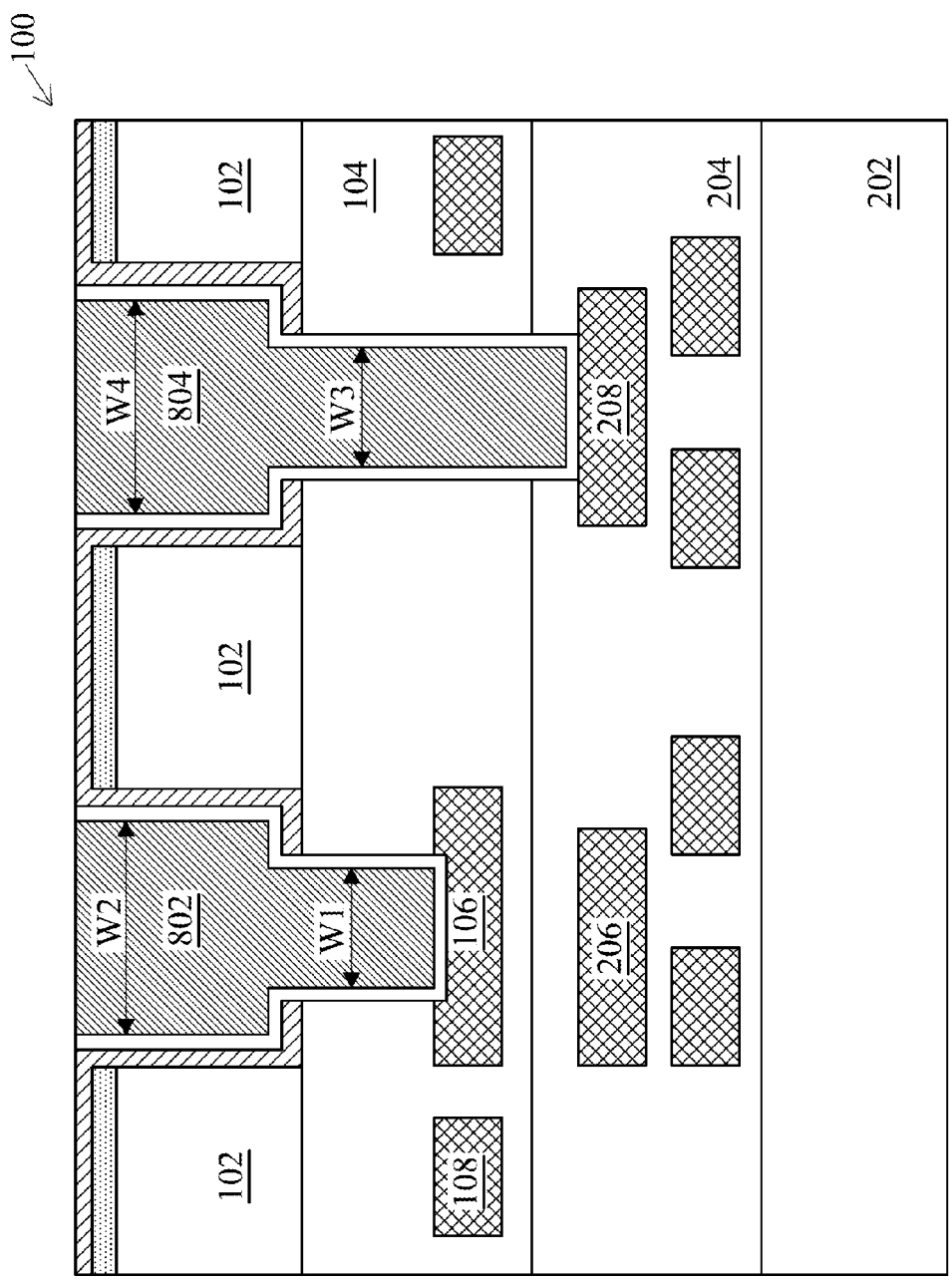
FIG. 8 illustrates a cross section view of the semiconductor device shown in FIG. 7 after a chemical mechanical polish (CMP) process is applied to the top surface of the semiconductor device in accordance with various embodiments of the present disclosure.

FIG. 8 illustrates a cross section view of the semiconductor device shown in FIG. 7 after a chemical mechanical polish (CMP) process is applied to the top surface of the semiconductor device in accordance with various embodiments of the present disclosure. A planarization process, such as CMP, etch back step and the like, may be performed to planarize the top surface of the semiconductor device. As shown in FIG. 8, a portion of the conductive material has been removed as a result. As shown in FIG. 8, there may be two conductive plugs 802 and 804 formed in the semiconductor device after the CMP process is performed on the semiconductor device.

As shown in FIG. 8, each conductive plug (e.g., conductive plugs 802 and 804) may comprise two portions. For the conductive plug 802, a first portion is from the hard mask layer to the front side of the first substrate 102. The first portion is of a width W1 as shown in FIG. 8. A second portion is from the front side of the first substrate 102 to the backside of the first substrate 102. The second portion is of a width W2 as shown in FIG. 8. In some embodiments, W2 is greater than or equal to W1.

For the conductive plug 804, a first portion is from the metal line 208 to the front side of the first substrate 102. The first portion is of a width W3 as shown in FIG. 8. A second portion is from the front side of the first substrate 102 to the backside of the first substrate 102. The second portion is of a width W4 as shown in FIG. 8. In some embodiments, W4 is greater than or equal to W3.

Figure 9:
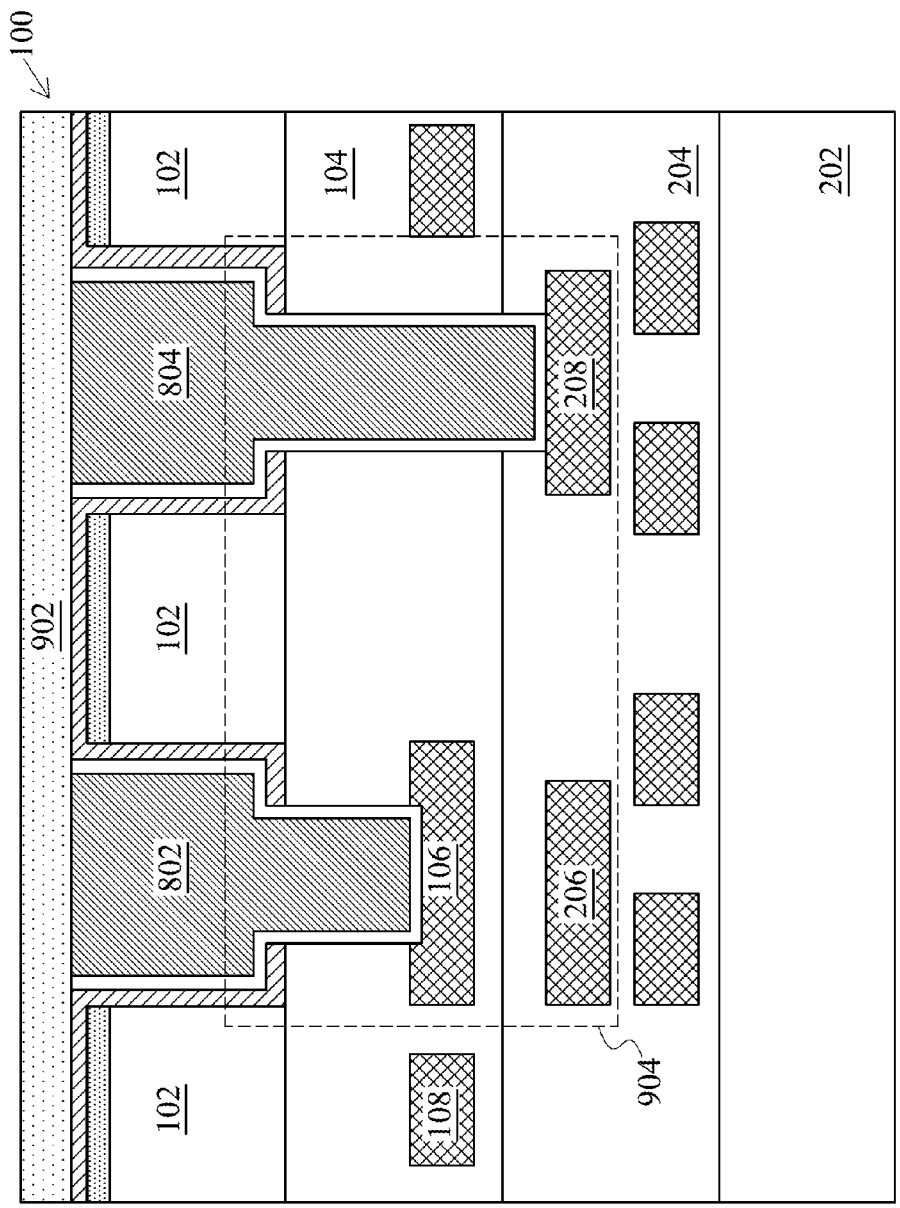
FIG. 9 illustrates a cross sectional view of the semiconductor device shown in FIG. 8 after a dielectric layer is formed on the semiconductor device in accordance with various embodiments of the present disclosure.

FIG. 9 illustrates a cross sectional view of the semiconductor device shown in FIG. 8 after a dielectric layer is formed on the semiconductor device in accordance with various embodiments of the present disclosure. The dielectric layer 902 may comprise commonly used dielectric materials, such as silicon nitride, silicon oxynitride, silicon oxycarbide, silicon carbide, combinations thereof, and multi-layers thereof. The dielectric layer 902 may be deposited over the semiconductor device through suitable deposition techniques such as sputtering, CVD and the like.

The conductive plugs (e.g., conductive plug 802) include two portions as described above with respect to FIG. 8. The conductive plugs 802 and 804 may be alternatively referred to as a three-dimensional structure 904 throughout the description.

One advantageous feature of the stacked wafer having the conductive plugs 802 and 804 shown in FIG. 9 is that the active circuits of both semiconductor wafers are connected to each other through a single conductive plug (e.g., conductive plug 804). Such a single conductive plug helps to further reduce form factor.

Alternatively, the active circuits of both semiconductor wafers are connected to each other through two conductive plugs and a connection structure such as a metal coupled between two conductive plugs. The detailed connection structure of the conductive plugs will be described below with respect to FIG. 13 and FIG. 14.

In sum, in comparison to stacked semiconductor devices connected by multiple conductive plugs, the single conductive plug (e.g., conductive plug 804) coupled between two semiconductor wafers shown in FIG. 9 helps to cut power consumption and prevent parasitic interference.

It should be noted while FIG. 9 illustrates two semiconductor wafers stacked together, one skilled in the art will recognize that the stacked semiconductor device shown in FIG. 9 is merely an example. There may be many alternatives, variations and modifications. For example, the stacked semiconductor device may accommodate more than two semiconductor wafers.

Figure 10:
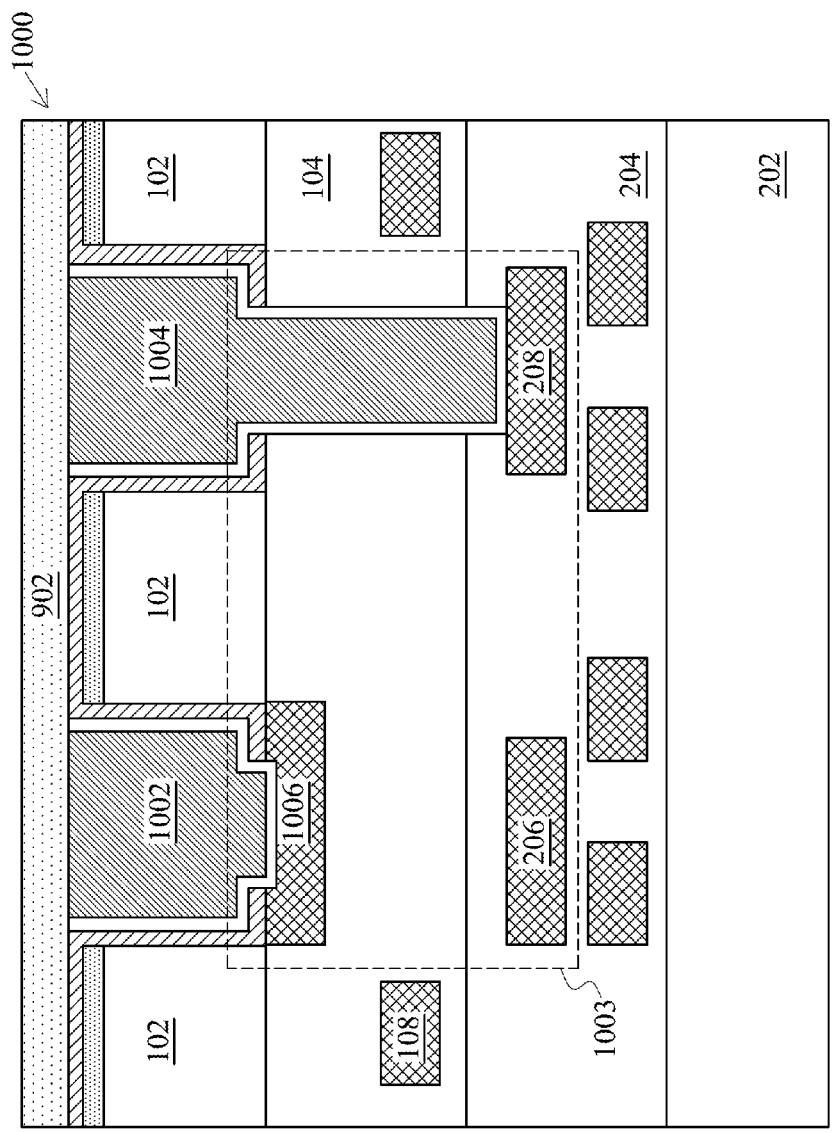
FIG. 10 illustrates a cross sectional view of another stacked semiconductor device in accordance with various embodiments of the present disclosure.

FIG. 10 illustrates a cross sectional view of another stacked semiconductor device in accordance with various embodiments of the present disclosure. The stacked semiconductor device 1000 is similar to the stacked semiconductor device 100 shown in FIG. 9 except that the hard mask layer is formed by contacts, which is located adjacent to the interface between the first substrate 102 and the inter-metal dielectric layers 104.

The contacts may be formed in an inter-layer dielectric layer (not shown). The inter-layer dielectric layer may comprise a material such as boron phosphorous silicate glass (BPSG), although any suitable dielectrics may be used for either layer. The inter-layer dielectric layer may be formed using a process such as PECVD, although other processes may alternatively be used.

The contact 1006 may be formed through the inter-layer dielectric layer with suitable photolithography and etching techniques. Generally, these photolithography techniques involve depositing a photoresist material, which is masked, exposed, and developed to expose portions of the inter-layer dielectric layer that are to be removed. The remaining photoresist material protects the underlying material from subsequent processing steps, such as etching.

The contact 1006 may comprise a barrier/adhesion layer (not shown) to prevent diffusion and provide better adhesion for the contact 1006. In some embodiments, the contact 1006 may be formed of any suitable conductive material, such as a highly-conductive, low-resistive metal, elemental metal, transition metal, or the like.

In accordance with an embodiment, the contact 1006 may be formed of tungsten, although other materials, such as copper, aluminum and/or the like, could alternatively be utilized. In an embodiment in which the contact 1006 is formed of tungsten, the contact 1006 may be deposited by CVD techniques known in the art, although any method of formation could alternatively be used.

As shown in FIG. 10, the conductive plugs (e.g., conductive plugs 1002 and 1004) include two portions. The conductive plugs may be alternatively referred to as a three-dimensional structure 1003 throughout the description.

Figure 11:
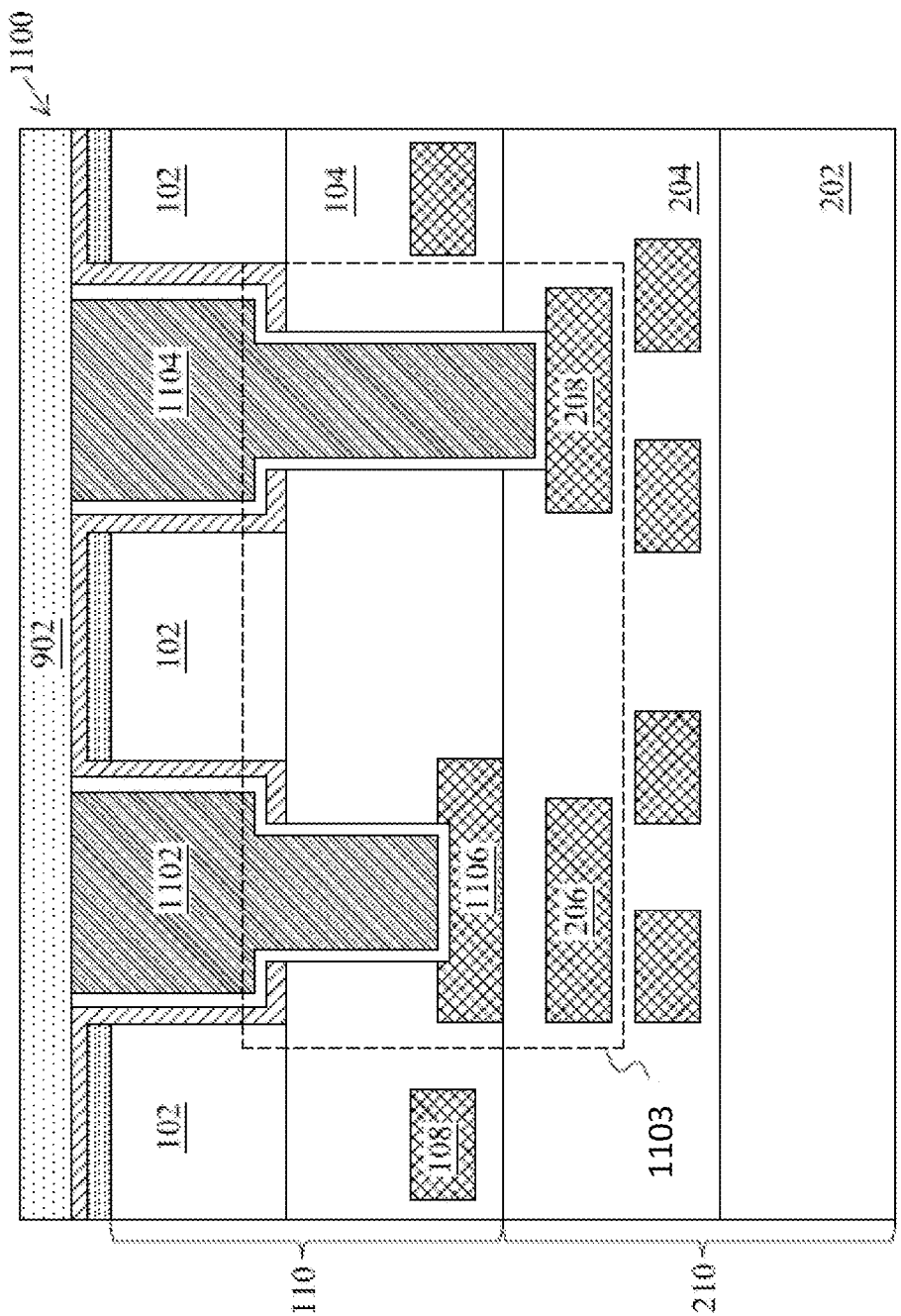
FIG. 11 illustrates a cross sectional view of yet another stacked semiconductor device in accordance with various embodiments of the present disclosure.

FIG. 11 illustrates a cross sectional view of yet another stacked semiconductor device in accordance with various embodiments of the present disclosure. The stacked semiconductor device 1100 is similar to the stacked semiconductor device 100 shown in FIG. 9 except that the etching hard mask is formed by redistribution lines, which are located adjacent to the interface of two semiconductor wafers.

The redistribution line 1106 may be a single material layer, or a multi-layered structure and may be made of metals such as titanium, titanium nitride, aluminum, tantalum, copper and combinations thereof. The redistribution line 1106 may be made by any suitable method known in the art such as physical vapor deposition (PVD), sputter, CVD, electroplating and/or the like.

The conductive plugs (e.g., conductive plugs 1102 and 1104) include two portions. The conductive plugs may be alternatively referred to as a three-dimensional structure 1103 throughout the description.

It should be noted that the first semiconductor wafer 110 may be bonded on the second semiconductor wafer 210 through a suitable metal-dielectric bonding technique such as a copper-silicon oxide nitride (Cu—SiON) bonding process.

It should further be noted while FIG. 9, FIG. 10 and FIG. 11 illustrate hard mask layers formed by metal lines, contacts and redistribution lines respectively, one skilled in the art will recognize that hard mask layers shown in FIGS. 9-11 are merely examples. There may be many alternatives, variations and modifications. For example, the hard mask layer may be formed by a plurality of isolation regions, poly-silicon regions, any combinations thereof and/or the like.

Figure 12:
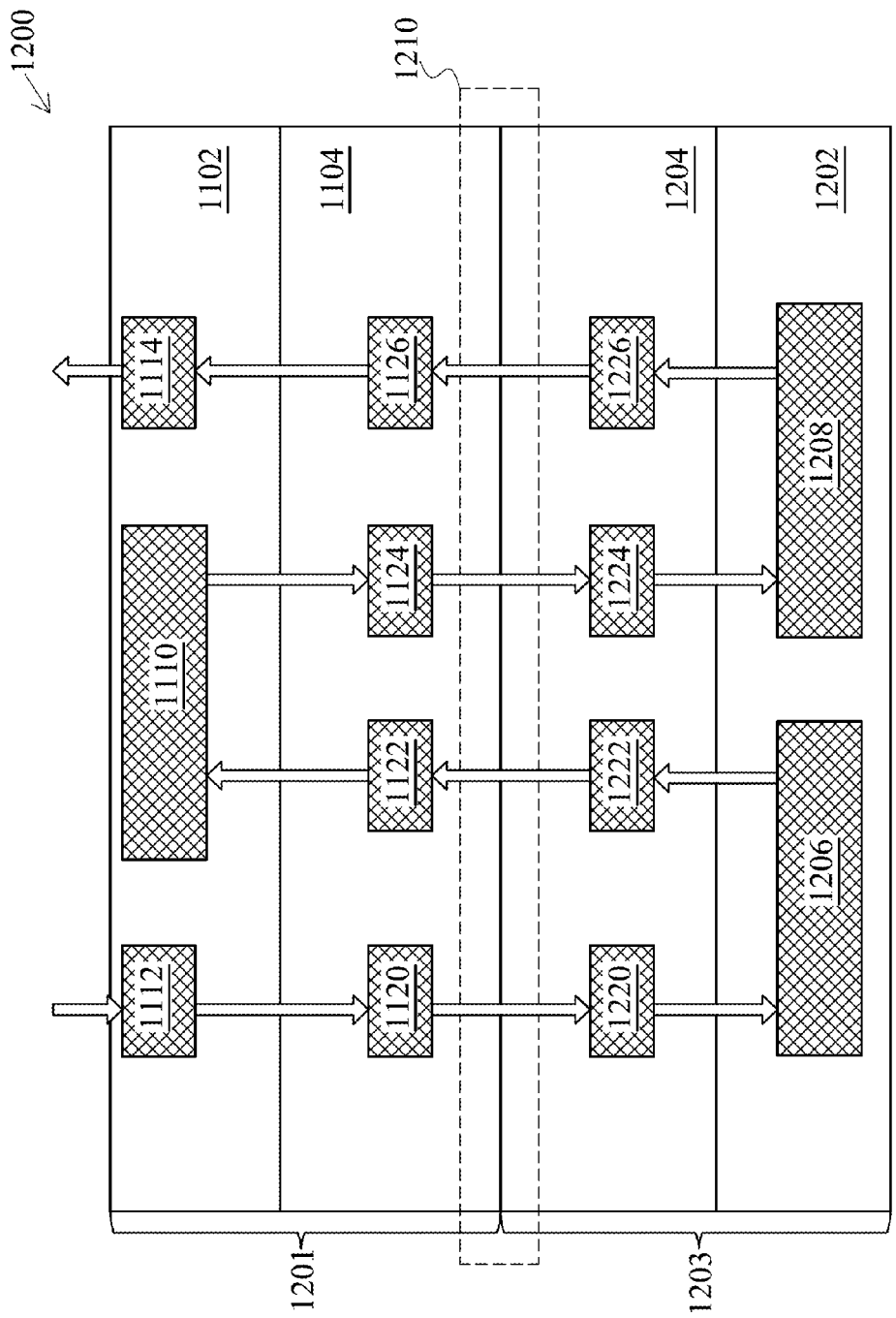
FIG. 12 illustrates a cross sectional view of a backside illuminated imager sensor including a stacked wafer structure in accordance with various embodiments of the present disclosure.

FIG. 12 illustrates a cross sectional view of a backside illuminated imager sensor including a stacked wafer structure in accordance with various embodiments of the present disclosure. The backside illuminated image sensor 1200 comprises two semiconductor wafers, namely a sensor wafer 1201 and an application-specific integrated circuit (ASIC) wafer 1203. As shown in FIG. 12, the sensor wafer 1201 is stacked on top of the ASIC 1203. In some embodiments, the sensor wafer 1201 and the ASIC wafer 1203 are connected to each other through suitable three-dimensional structures such as the three-dimensional structure 904 shown in FIG. 9, the three-dimensional structure 1003 shown in FIG. 10, the three-dimensional structure 1103 shown in FIG. 11 and any combinations thereof.

The ASIC wafer 1203 may comprise a plurality of logic circuits such as logic circuits 1206 and 1208. In some embodiments, the logic circuits may be an analog-to-digital converter. However, the logic circuits may be other functional circuits that may be utilized within a backside illuminated image sensor. For example, the logic circuits 1206 and 1208 may be a data processing circuit, a memory circuit, a bias circuit, a reference circuit, any combinations thereof and/or the like.

The ASIC wafer 1203 may further comprise a plurality of interconnection layers and a plurality of metal lines 1220, 1222, 1224 and 1226 embedded in the interconnection layers. The metal lines 1220, 1222, 1224 and 1226 may function as interconnection structures. As indicated by the arrows shown in FIG. 12, the metal lines 1220, 1222, 1224 and 1226 provide signal paths between logic circuits 1206 and 1208, and the sensor wafer 1201.

The metal lines 1220, 1222, 1224 and 1226 may be made through any suitable formation process (e.g., lithography with etching, damascene, dual damascene, or the like) and may be formed using suitable conductive materials such as copper, aluminum, aluminum alloys, copper alloys or the like.

The sensor wafer 1201 is fabricated by CMOS process techniques known in the art. In particular, the sensor wafer

1201 comprises an epitaxial layer over a silicon substrate. According to the fabrication process of backside illuminated image sensors, the silicon substrate has been removed in a backside thinning process until the epitaxial layer is exposed. A portion of epitaxial layer may remain. A p-type photo active region and an n-type photo active region (not shown respectively) are formed in the remaining epitaxial layer.

The photo active regions such as the p-type photo active region and the n-type photo active region may form a PN junction, which functions as a photodiode. As shown in FIG. 12, the imager sensor 1110 may comprise a plurality of photodiodes.

The sensor wafer 1201 may comprise a transistor (not shown). In particular, the transistor may generate a signal related to the intensity or brightness of light that impinges on the photo active regions. In accordance with an embodiment, the transistor may be a transfer transistor. However, the transistor may be an example of the many types of functional transistors that may be utilized within a backside illuminated image sensor. For example, the transistor may include other transistors located within a backside illuminated image sensor, such as a reset transistor, a source follower transistor or a select transistor. All suitable transistors and configurations that may be utilized in an image sensor are fully intended to be included within the scope of the embodiments.

The sensor wafer 1201 may comprise a plurality of interconnection layers and metal lines embedded in the interconnection layers. The metal lines 1120, 1122, 1124 and 1126 may provide signal paths between the sensor wafer 1201 and the ASIC wafer 1203. In particular, as indicated by the arrows shown in FIG. 12, an external signal may enter the backside illuminated image sensor 1200 through the aluminum copper pad 1112, and then reach the metal routing (e.g., metal line 1120) through interconnect structures such through vias (not shown). The external signal may further pass through a three-dimensional structure 1210. The three-dimensional structure 1210 may be the three-dimensional structure 904 shown in FIG. 9, the three-dimensional structure 1003 shown in FIG. 10, the three-dimensional structure 1103 shown in FIG. 11 and/or any combinations thereof.

After the external signal passes the three-dimensional structure 1210, the external signal may reach the logic circuit 1206 through the metal routing (e.g., metal line 1220) of the ASIC wafer 1203.

When a signal leaves the logic circuit 1206, it reaches the image sensor 1110 through a conductive path formed by the metal routing (e.g., metal line 1222) of the ASIC wafer 1203, the three-dimensional structure 1210, the metal routing (e.g., metal line 1122) of the sensor wafer 1201.

After the image sensor 1110 generates a signal, the signal is sent to the logic circuit 1208 through a path formed by the metal routing (e.g., metal line 1124) of the sensor wafer 1201, the three-dimensional structure 1210, the metal routing (e.g., metal line 1224) of the ASIC wafer 1203. Furthermore, the signal may be sent outside of the backside illuminated image sensor 1200 from the logic circuit 1208 through a path formed by the metal routing (e.g., metal line 1226) of the ASIC wafer 1203, the three-dimensional structure 1210, the metal routing (e.g., metal line 1126) of the sensor wafer 1201 and the aluminum copper pad 1114.

The logic circuit 1206 and 1208 may be coupled to aluminum copper pads 1112 and 1114. As shown in FIG. 12, the aluminum copper pads 1112 and 1114 may be formed on the backside of the sensor wafer 1201.

It should be noted that the location of the aluminum copper pads 1112 and 1114 shown in FIG. 12 is merely an example. A person skilled in the art will recognize that there may be many alternatives, modifications and variations. For example, the aluminum copper pads 1112 and 1114 may be formed on the non-bonding side of the ASIC wafer 1203. The form factor of a backside illuminated image sensor can be reduced by forming the aluminum copper pads 1112 and 1114 on the non-bonding side of the ASIC wafer 1203.

One advantageous feature of having input/output terminals formed on the non-bonding side of the ASIC wafer 1203 is that the density as well as quantum efficiency of the backside illuminated image sensor 1200 can be improved as a result.

Figure 13:
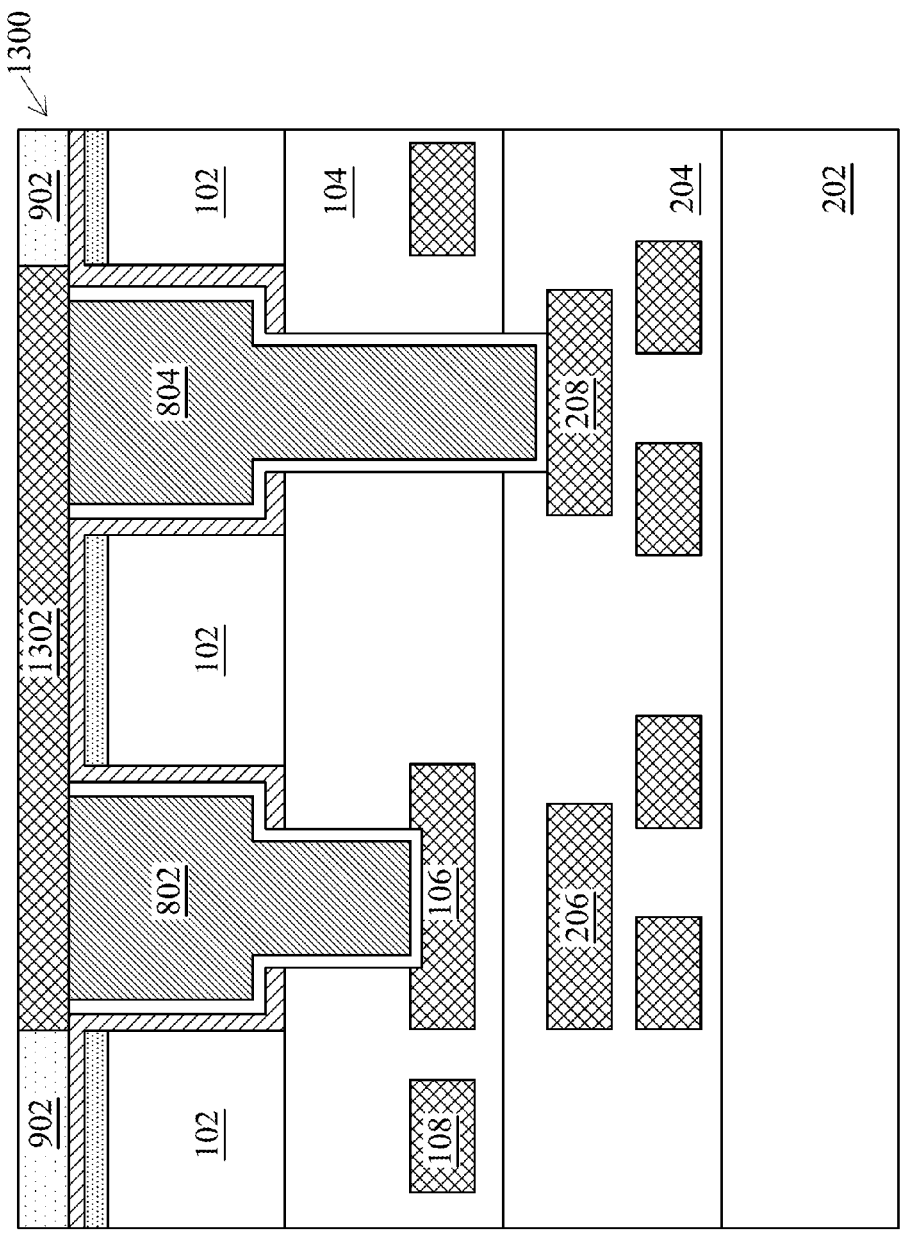
FIG. 13 illustrates a connection structure of the dual pads in accordance with various embodiments of the present disclosure.

FIG. 13 illustrates a connection structure of the dual pads in accordance with various embodiments of the present disclosure. The active circuits of the first semiconductor wafer and the active circuits of the second semiconductor wafer may be connected to each other through two conductive plugs 802 and 804, and a metal line 1302 coupled between two conductive plugs. The metal line 1302 may be formed of suitable conductive materials such as Tungsten (W), Aluminum Copper (ALCu) and/or the like.

Figure 14:
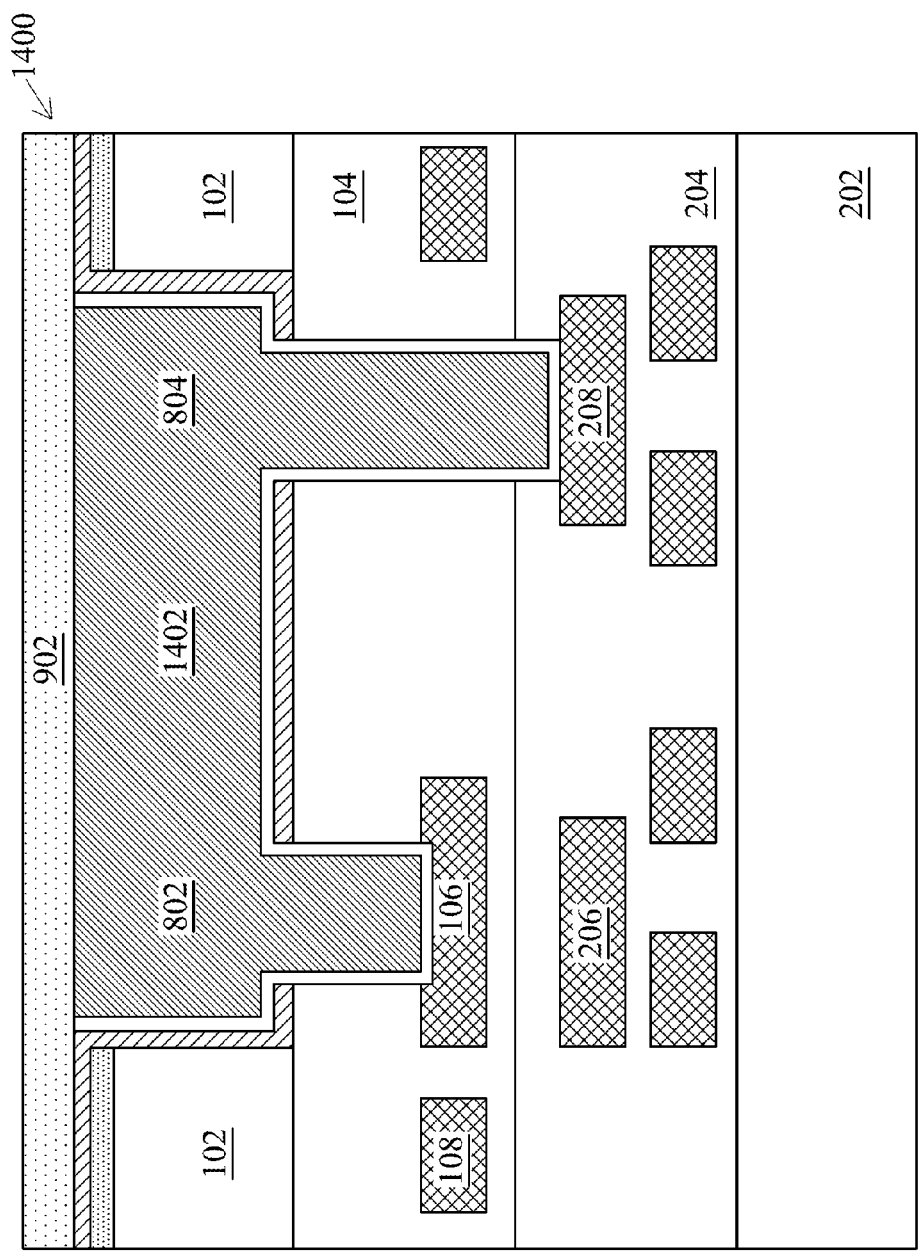
FIG. 14 illustrates another connection structure of the dual pads in accordance with various embodiments of the present disclosure.

FIG. 14 illustrates another connection structure of the dual pads in accordance with various embodiments of the present disclosure. The active circuits of the first semiconductor wafer and the active circuits of the second semiconductor wafer may be connected to each other through two conductive plugs 802 and 804, and a connection structure 1402 coupled between two conductive plugs. The connection structure 1402 may be formed of copper and formed in the first substrate 102 as shown in FIG. 14.

Figure 17:
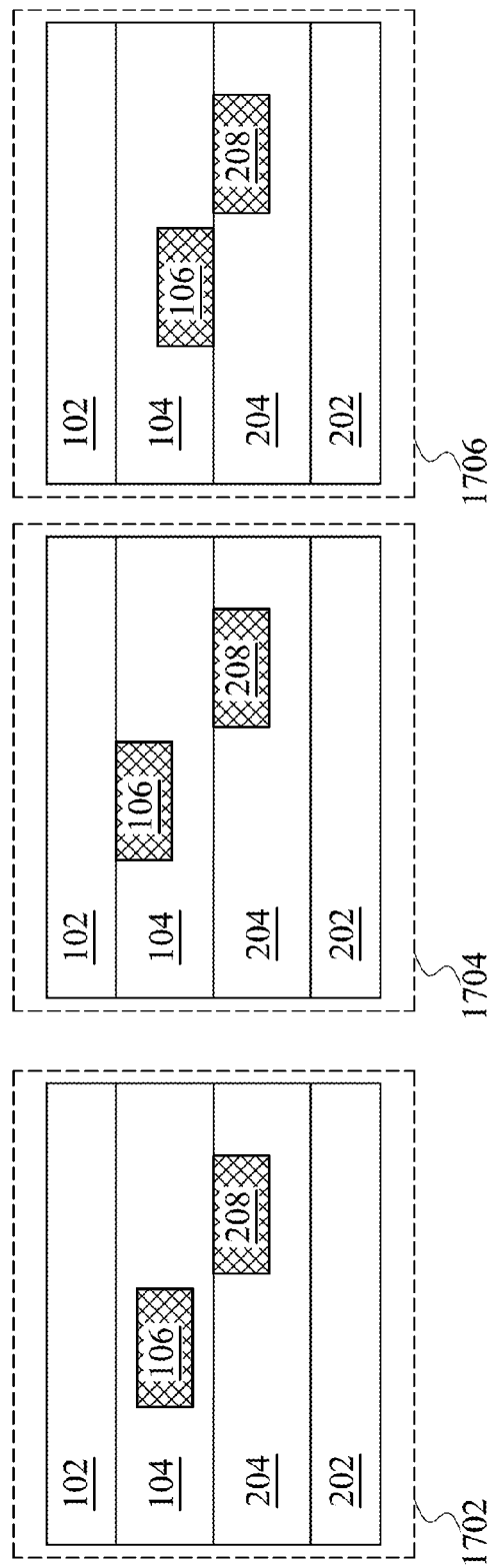
FIG. 17 illustrates a plurality of third combinations of the dual pads in accordance with various embodiments of the present disclosure.

FIG. 13 and FIG. 14 show the locations of the hard mask layers (e.g., metal lines 106 and 208). A person skilled in the art will recognize there may be many alternatives, variations and modifications. FIGS. 15-17 will illustrate various embodiments including different combinations of the hard mask layers. Throughout the description, the hard mask layer located in the first semiconductor wafer 110 (e.g., metal line 106) may be alternatively referred to as a first pad. Likewise, the hard mask layer located in the second semiconductor wafer 210 (e.g., metal line 208) may be alternatively referred to as a second pad.

FIGS. 15-17 illustrate some examples. However, as one having ordinary skill in the art will recognize, the combinations described below are merely exemplary pad configurations and are not meant to limit the current embodiments.

FIG. 15 illustrates a plurality of first combinations of the dual pads in accordance with various embodiments of the present disclosure.

The cross sectional view 1502 shows the first pad 106 is a metal line in the inter-metal dielectric layer 104. The second pad 208 is a metal line in the inter-metal dielectric layer 204.

The cross sectional view 1504 shows that the first pad 106 is a contact in the inter-metal dielectric layer 104. The second pad 208 is a metal line in the inter-metal dielectric layer 204.

The cross sectional view 1506 shows that the first pad 106 is a redistribution line in the inter-metal dielectric layer 104. The second pad 208 is a metal line in the inter-metal dielectric layer 204.

FIG. 16 illustrates a plurality of second combinations of the dual pads in accordance with various embodiments of the present disclosure. The cross sectional view 1602 shows the first pad 106 is a metal line in the inter-metal dielectric layer 104. The second pad 208 is a contact in the inter-metal dielectric layer 204.

The cross sectional view 1604 shows that the first pad 106 is a contact in the inter-metal dielectric layer 104. The second pad 208 may be a contact in the inter-metal dielectric layer 204.

The cross sectional view 1606 shows that the first pad 106 is a redistribution line in the inter-metal dielectric layer 104. The second pad 208 is a contact in the inter-metal dielectric layer 204.

FIG. 17 illustrates a plurality of third combinations of the dual pads in accordance with various embodiments of the present disclosure. The cross sectional view 1702 shows that the first pad 106 is a metal line in the inter-metal dielectric layer 104. The second pad 208 is a redistribution line in the inter-metal dielectric layer 204.

The cross sectional view 1704 shows that the first pad 106 is a contact in the inter-metal dielectric layer 104. The second pad 208 is a redistribution line in the inter-metal dielectric layer 204.

The cross sectional view 1706 shows that the first pad 106 is a redistribution line in the inter-metal dielectric layer 104. The second pad 208 is a redistribution line in the inter-metal dielectric layer 204.

In accordance with an embodiment, an apparatus comprises a first semiconductor chip including a first substrate and a plurality of first interconnect components formed over the first substrate, a second semiconductor chip bonded on the first semiconductor chip, wherein the second semiconductor chip comprises a second substrate and a plurality of second interconnect components formed over the second substrate, a first conductive plug coupled to a first interconnect component and a second conductive plug coupled to a second interconnect component.

The first conductive plug comprises a first portion formed between the first interconnect component and a front side of the first substrate, and wherein the first portion is of a first width and a second portion formed between the front side of the first substrate and a backside of the first substrate, wherein the second portion is of a second width greater than or equal to the first width.

The second conductive plug comprises a third portion formed between the second interconnect component and the front side of the first substrate, and wherein the third portion is of a third width and a fourth portion formed between the front side of the first substrate and the backside of the first substrate, wherein the fourth portion is of a fourth width greater than or equal to the third width.

In accordance with an embodiment, a device comprises a first chip comprising a first substrate and a plurality of first interconnect components formed in first inter-metal dielectric layers and over the first substrate, a second chip bonded on the first chip, wherein the second chip comprises a second substrate and a plurality of second interconnect components formed in second inter-metal dielectric layers and over the second substrate.

The device further comprises a first conductive plug formed through the first substrate and formed partially through the first inter-metal dielectric layers, wherein the first conductive plug is coupled to a first interconnect component and a second conductive plug formed through the first substrate and the first inter-metal dielectric layers and formed partially through the second inter-metal dielectric layers, wherein the second conductive plug is coupled to a second interconnect component.

In accordance with an embodiment, a method comprises bonding a first semiconductor wafer on a second semiconductor wafer, wherein the first semiconductor wafer comprises a first substrate, first inter-metal dielectric layers and first interconnect structures formed in the first inter-metal dielectric layers and over the first substrate and the second semiconductor wafer comprises a second substrate, second inter-metal dielectric layers and second interconnect structures formed in the second inter-metal dielectric layers and over the second substrate and patterning the first substrate to form a first opening and a second opening in the first substrate.

The method comprises forming a third opening and a fourth opening using an etching process and using a first interconnect structure as a hard mask layer, wherein the third opening is an extension of the first opening and formed partially through the first inter-metal dielectric layers and the fourth opening is an extension of the second opening and formed through the first inter-metal dielectric layers and partially through the second inter-metal dielectric layers and plating a conductive material in the first opening, the second opening, the third opening and the fourth opening to form a first conductive plug and a second conductive plug.

Although embodiments of the present invention and its advantages have been described in detail, it should be understood that various changes, substitutions and alterations can be made herein without departing from the spirit and scope of the invention as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device comprising:
  a first chip comprising:
    a first substrate; and
    a plurality of first interconnect components formed in a first inter-metal dielectric layer and over the first substrate;
  a second chip bonded on the first chip, wherein the second chip comprises:
    a second substrate; and
    a plurality of second interconnect components formed in a second inter-metal dielectric layer and over the second substrate, and wherein a top surface of the second inter-metal dielectric layer is in direct contact with a top surface of the first inter-metal dielectric layer;
  a first conductive plug having a substrate portion formed through the first substrate and a non-substrate portion formed partially through the first inter-metal dielectric layer, wherein the first conductive plug is coupled to a first interconnect component, wherein a width of the substrate portion of the first conductive plug is greater than a width of the non-substrate portion of the first conductive plug, and the substrate portion of the first conductive plug and the non-substrate portion of the first conductive plug are formed of a same material, and wherein the first conductive plug extends into the first interconnect component;

a second conductive plug having a first portion formed through the first substrate and the first inter-metal dielectric layer, and a second portion formed partially through the second inter-metal dielectric layer, wherein the second conductive plug is coupled to a second interconnect component, wherein a width of a substrate portion of the second conductive plug is greater than a width of a non-substrate portion of the second conductive plug, and the first portion of the second conductive plug and the second portion of the second conductive plug are formed of a same material, wherein the second conductive plug is physically separated from each conductive component within the first inter-metal dielectric layer; and a dielectric liner extending from a first point between the substrate portion of the first conductive plug and the first substrate to a second point between the substrate portion of the second conductive plug and the first substrate, wherein a sidewall surface of the non-substrate portion of the first conductive plug is free from the dielectric liner, wherein the dielectric liner comprises a first material throughout the dielectric liner.

2. The device of claim 1, wherein:
the first chip comprises a backside illuminated image sensor; and
the second chip comprises a plurality of logic circuits.

3. The device of claim 1, wherein:
the first interconnect component is a first metal line formed in the first inter-metal dielectric layer; and
the second interconnect component is a second metal line formed in the second inter-metal dielectric layer.

4. The device of claim 1, wherein:
the first interconnect component is a first redistribution line formed over the first substrate; and
the second interconnect component is a second metal line formed in the second inter-metal dielectric layer.

5. The semiconductor device of claim 1, further comprising a bottom anti-reflective layer located between the dielectric liner and the first substrate, wherein the first conductive plug extends into the first interconnect component with planar sidewalls.

6. A device comprising:
a first chip comprising a plurality of first interconnect components in a first interconnect portion over a first substrate;
a second chip comprising a plurality of second interconnect components in a second interconnect portion over a second substrate, wherein the second interconnect portion of the second chip is bonded on and in direct contact with the first interconnect portion of the first chip;
a first conductive plug formed through the first substrate and formed partially through the first interconnect portion, wherein the first conductive plug is coupled to a first interconnect component, and wherein a substrate portion and a non-substrate portion of the first conductive plug are formed of a same material, wherein the first conductive plug extends into the first interconnect component, wherein the substrate portion has a first width and the non-substrate portion has a second width smaller than the first width;
a liner covering sidewalls of the substrate portion but not sidewalls of the non-substrate portion, the liner extending over an anti-reflective coating; and
a second conductive plug formed through the first substrate and the first interconnect portion, and formed partially through the second interconnect portion, wherein the second conductive plug is coupled to a second interconnect component, and wherein a substrate portion and a non-substrate portion of the second conductive plug are formed of a same material.

7. The device of claim 6, wherein:
the first interconnect portion comprises a plurality of first inter-metal dielectric layers over the first substrate.

8. The device of claim 6, wherein:
the second interconnect portion comprises a plurality of second inter-metal dielectric layers over the first substrate.

9. The device of claim 6, wherein:
the first interconnect component is a first metal line in the first interconnect portion; and
the second interconnect component is a second metal line in the second interconnect portion.

10. The device of claim 6, wherein:
the first interconnect component is a first metal line in the first interconnect portion; and
the second interconnect component is a contact in the second interconnect portion.

11. The device of claim 6, wherein:
the first interconnect component is a first metal line in the first interconnect portion; and
the second interconnect component is a redistribution line in the second interconnect portion.

12. A semiconductor device comprising:
a first chip comprising a first substrate and a first bonding layer disposed over the first substrate, wherein the first chip comprises a first interconnect component;
a second chip comprising a second substrate and a second bonding layer disposed there-over, wherein the second chip comprises a second interconnect component, and wherein the first and the second chips are bonded through contact between the first and the second bonding layers that defines a continuous joining interface there-between;
a first type conductive plug accessibly formed in the first substrate and connecting the first interconnect component without extending through the continuous joining interface, wherein a lower portion of the first type conductive plug extends into the first interconnect component, wherein the first type conductive plug further comprises:
a first portion formed between the first interconnect component and an interface between the first bonding layer and the first substrate, and wherein the first portion has a first constant width as the first portion extends into the first interconnect component; and
a second portion formed between the interface and a non-bonding side of the first substrate, and wherein the second portion is of a second width greater than the first width; and
a second type conductive plug accessibly formed in the first substrate and extending through the continuous joining interface to connect the second interconnect component without penetrating through the second bonding layer.

13. The semiconductor device of claim 12, wherein:
the first type conductive plug is connected to the second type conductive plug through a metal line formed over a non-bonding side of the first substrate, and wherein the metal line and the first interconnect component are on opposite sides of the first substrate.

14. The semiconductor device of claim 12, wherein the second type conductive plug comprises:
 a third portion formed between the second interconnect component and the interface, and wherein the third portion is of a third width; and
 a fourth portion formed between the interface and the non-bonding side of the first substrate, wherein the fourth portion is of a fourth width greater than the third width.

15. The semiconductor device of claim 14, wherein:
the fourth portion and the third portion of the second type conductive plug are on opposite sides of the interface.

16. The semiconductor device of claim 12, wherein:
sidewalls of the first type conductive plug are enclosed by a first barrier layer, and wherein the first barrier layer is a first continuous layer extending from a non-bonding side of the first substrate to the first interconnect component; and
the first barrier layer and the first substrate are separated by a first dielectric layer, and wherein the first dielectric layer extends from the non-bonding side of the first substrate to a bonding side of the first substrate, and wherein the first dielectric layer is over the non-bonding side of the first substrate without extending into the first bonding layer.

17. The semiconductor device of claim 16, wherein:
sidewalls of the second type conductive plug are enclosed by a second barrier layer, and wherein the second barrier layer is a second continuous layer extending from a non-bonding side of the first substrate to the second interconnect component, and wherein the second barrier layer extends through the continuous joining interface; and
the second barrier layer and the first substrate are separated by a second dielectric layer, and wherein the second dielectric layer extends from the non-bonding side of the first substrate to a bonding side of the first substrate, and wherein the second dielectric layer is over the non-bonding side of the first substrate without extending into the first bonding layer, and wherein a bottom surface of the second dielectric layer is substantially level with a bottom surface of the first dielectric layer.

* * * * *